United States Patent [19]

Sturm

[11] Patent Number: 4,965,452

[45] Date of Patent: Oct. 23, 1990

[54] INFRARED ANALYSIS OF PAPER PRINTABILITY

[75] Inventor: Steven P. Sturm, Columbus, Ohio

[73] Assignee: Process Automation Business, Inc., Columbus, Ohio

[21] Appl. No.: 410,790

[22] Filed: Sep. 22, 1989

Related U.S. Application Data

[63] Continuation-in-part of Ser. No. 217,185, Jul. 11, 1988.

[51] Int. Cl.$^5$ ............................................. G01N 21/35
[52] U.S. Cl. ................................... 250/339; 250/341; 250/359.1
[58] Field of Search ..................... 250/339, 341, 358.1, 250/359.1

[56] References Cited

U.S. PATENT DOCUMENTS 4,124,803  11/1978  Bowers ................................. 250/341

Primary Examiner—Carolyn E. Fields
Attorney, Agent, or Firm—John H. Mulholland

[57] ABSTRACT

The printability of paper coated with kaolinite clay is dependent upon the flatness of kaolinite alumino-silicate clay platelets on the surface thereof. The flatness is determined by calculating the ratio of two infrared absorption bands from two specific types of structural hydroxyls characteristic of kaolinite clay platelet crystals.

4 Claims, 1 Drawing Sheet

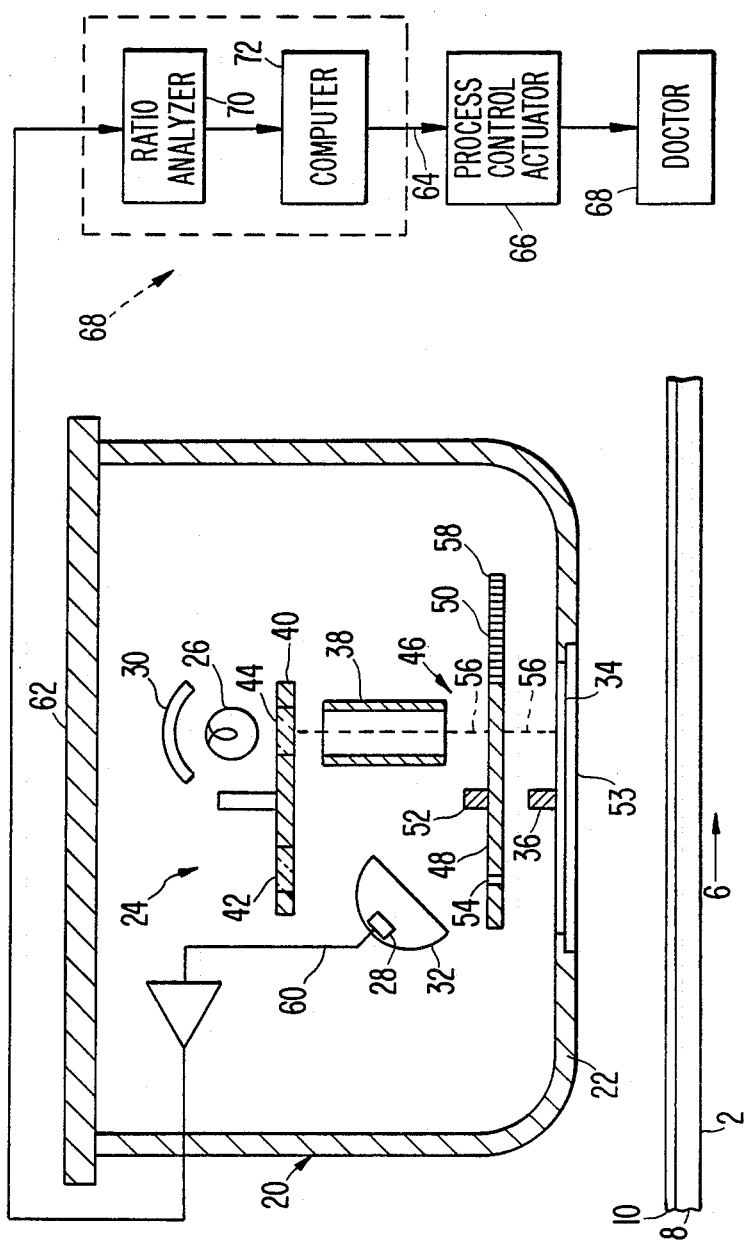

INFRARED ANALYSIS OF PAPER PRINTABILITY

RELATED APPLICATION

This application is a continuation-in-part of U.S. patent application Ser. No. 217,185, filed July 11, 1988.

This invention relates generally to process measurements and automation within the paper industry and, more particularly, to sensors used in process automation systems. Specifically, the present invention pertains to infrared-based sensors for use in determining the "flatness" of clay platelets on the surface of paper. Increased clay platelet flatness enhances smoothness and thus printability of paper.

It is a common practice in the paper industry to use sensors in measuring particular quality attributes of a sheet of paper product during its manufacture. The measurements are derived from data which are provided by the sensors. The magnitudes of the data depend on various physical properties of the sheet such as transmittance, reflectance, and emittance. Known relationships between the physical property and the quality attributes of interest are employed in the design of front-end electronics and software to derive measurements of the quality attributes from the data provided by the sensors. Examples of such quality attributes are moisture content, basis weight, thickness, ash content, gloss, color, opacity, formation, and brightness. The present invention adds to this list the quality attributes of printability or smoothness. A smooth clay coating prevents ink from spreading or draining through the paper fibers similar to an ink blotter's action on ink.

Once class of sensors (infrared-based sensors) employes the phenomenon of molecular resonance absorption to derive indications of the amount of a particular component which is contained in and on the paper. This class is most commonly used for deriving measurements of moisture content, although other applications such as the measurement of polymer content and fiber content are known. In a typical application, an indication of the content of a component is provided by determining the transmittance through or reflectance from the paper for two narrow bands of infrared radiation. One of these is typically designated a "measurement" or "absorption" band and is generally sensitive to absorption by the component of interest. The other is typically designated a "reference" band and is less sensitive to absorption by the same component. The ratio of the transmittances or reflectances of these two bands is related to the amount (typically, the weight per unit area) of the component which is contained in or on the paper. See U.S. Pat. Nos. 3,551,678 to Mitchell, and 3,405,268 to Brunton for examples of this approach. In the manufacture of some paper products, one or more filler-coater materials are added to enable the manufacturer to meet standards for certain quality attributes at a lower cost than would result if the standards were met by increasing the amount of more expensive materials contained in the paper. One of these filler-coater materials is clay. The type of clay ordinarily used in paper manufacturing is a hydrated aluminum silicate known as kaolin or its specie kaolinite. (Approximate compositions $Al_2O_3.2SiO_2.2H_2O$ and $Al_2Si_2O_5(OH)_4$, respectively.)

Kaolinite is a high-alumina mineral consisting of sheets of tetrahedrally coordinated silicon linked by an oxygen shared with octahedrally coordinated aluminum. It occurs with some vacant octahedral positions not filled with aluminum (or magnesium). There are two types of structural hydroxyls bound in the kaolinite crystals:

A first type of structural hydroxyls whose internuclear axes are inclined toward the vacant octahedral crystal positions relative to the silicate plane and a second type of structural hydroxyls whose internuclear axes are normal to the silicate plane.

It has been known for over fifty years that certain clay had distinct structural hydroxyl absorption bands determined by their crystalline locations and orientations. (Buswell, A. M., Krebs, K., and Rodebush, W. H., 1937, J. Amer. Chem. Soc. 59,2603.) Kaolin clay varies in quality, purity particle size and crystallinity, but is considered nominally to consist of 46 percent silicon dioxide, 39 percent aluminum oxide and 14 percent water. It's specie, kaolinite, can exist physically in both laminated structures and delaminated structures called platelets.

Infrared spectra of structural hydroxyl groups in clay materials show increasing absorption with an increasing angle of incidence of the light beam to the platelet surface. A fact which follows from established observations of Serratosa and Bradley, (1958); Serratosa, Hidalgo and Vivas, (1962); and Miller (1961) reported in Chapter 13 of *Infrared Spectra of Absorbed Species* by L. W. Little (pages 338-344). In that work it is stated at page 340 that: "Spectra measured for the dioctahedral mineral kaolinite (FIG. 145), show that the hydroxyls which are directed towards the vacant octahedral positions absorb at 3620 cm$^{-1}$ (2.762 microns) and the band intensity is independent of the orientation of the sample. The hydroxyls between the laminae in kaolinite are normal to the plate of the silicate sheet and absorb at 3710 cm$^{-1}$ (2.695 microns)." (Equivalents supplied.) Investigations made more recently, indicate that, depending on the clay's state of hydration and impurities, an absorption of 3695 cm$^{-1}$ (2.706) is a typical kaolinite reading for hydroxyls between the laminae.

The absorption band due to the latter or second type of structural hydroxyls is quite sensitive to the direction of the incoming radiation. A molecular vibration which involves a changing dipole moment along the direction of the incident infrared radiation will not interact with the electric vector of the radiation. (L. H. Little, supra, Chapter 10.)

SUMMARY OF THE INVENTION

The determination of kaolinite platelet relative "flatness" on kaolinite clay coated paper to determine printability of the paper is accomplished by the apparatus and method of the invention.

The apparatus and method include a determination of relative platelet flatness by measurement of the orientation of the clay platelets on the paper substrate. This is an indication of printability and is determined by calculating the ratio of the absorption bands from the two specific types of structural hydroxyls which are characteristic of kaolinite clay platelet crystals, namely a first type of hydroxyls whose internuclear axes are inclined toward vacant octahedral crystal positions relative to the silicate plane and a second type of hydroxyls whose internuclear axes are normal to the silicate plane.

The sensor used may be either those commonly termed "transmission" because they indicate radiation not absorbed but transmitted through the paper web or substrate and any coating thereon or those commonly called "reflection" because they sense radiation impinged upon the coating without being absorbed. Reflection sensors are preferred for this invention. An example of such a device and how it can control processing is disclosed in my co-pending U.S. patent application Ser. No. 217,185 filed July 11, 1988.

The apparatus of the method of the invention involves, then, measuring the relative flatness of kaolinite clay platelets on a substrate, using the two separate types of characteristic structural hydroxyls of the kaolinite. After measuring the radiation absorption of each of the two-types of and a computer, the ratio of one to the other is calculated to determine relative flatness of the clay platelets on the substrate surface.

BRIEF DESCRIPTION OF THE DRAWINGS

FIG. 1 is a generally schematic illustration of the preferred embodiment of the invention.

DESCRIPTION OF THE PREFERRED EMBODIMENT

Referring to FIG. 1, a sheet 2 of paper is illustrated as moving in a direction indicated by the arrow 6. The sheet 2 has a substrate layer 8 and a kaolinite clay platelet coating layer 10.

The numeral 20 designates a sensor that employs a reflection geometry in measuring the radiation absorption of clay platelets' two types of structural hydroxyls of the coating layer 10. For products which are coated on both sides of the sheet, an additional sensor incorporating the teaching herein would be positioned on the opposite side of the sheet so that absorption could be measured for each coating layer's structural hydroxyls.

In operation, the sensor 20 is installed in a scanner (not shown) mounted on a conventional sheet-traversing structure (not shown), so that measurements can be repeatedly derived for a plurality of cross-directional positions of the sheet 2.

Referring to FIG. 1, the sensor comprises a housing 22 for a source/detector arrangement 24 which includes an infrared source lamp 26 and a photodetector 28. The lamp 26 is positioned approximately along the focal line of a parabolic reflector 30, and the photodetector is positioned at approximately the focus of a parabolic collector 32. The axes of the reflector 30 and the collector 32 are separated at an angle of about thirty degrees, and the entire source/detector arrangement 24 may be tilted at angles from 0 to 70 degrees with respect to an imaginary line extending vertically upward or normal from the sheet 2.

A circular glass plate 34 cemented to the housing 22 provides a window and dust carrier. Secured to the inside of the housing 22 and abutting the plate 34 is a first light shield 36. A collimator 38 positioned between a filter wheel 40 and the plate 34 directs radiation transmitted through the filter wheel to the sheet 2. Installed in the filter wheel 40 are at least two but preferably four filters selected to pass narrow bands of infrared radiation as further described below. The filter wheel 40 is driven by a synchronous motor (not shown) and is positioned such that the filters installed therein (as at 42 and 44) successively pass through the radiation path between the lamp 26 and the collimator 38. At least two optical filters are installed in the wheel 40 at equally-spaced intervals. Each filter passes a narrow band of infrared radiation. One filter 42 passes a kaolinite measurement band having a center wavelength absorption range centered at about 2.706 microns. Another filter 44 passes a kaolinite band having a center wavelength absorption range centered at about 2.762 microns. These represent the two types of kaolinite structural hydroxyls, as discussed above.

A generally L-shaped standardization mechanism 46 is provided and includes a pivot arm 48 to which a standardization flag 50 and a second light shield 52 are secured. The mechanism 46 is rotatable about an axis 54 so that during the standardization mode the flag 50 is positioned in the radiation path 56 between the collimator 38 and the plate 34. The second light shield 52 is positioned so that during the measurement mode it cooperates with the first light shield 36 to block radiation reflected from dust which may accumulate on the outer surface 53 of the plate 34, but during the standardization mode permits passage of radiation from the diffuse surface 58 of the flag 50 to the collector 32 by actuating a solenoid (not shown) to rotate the standardization mechanism 46 about the axis 54.

The infrared source 26 may be any source which emits infrared over a spectral band which includes all narrow bands selected for practicing this invention, as further described below. A 375-watt tungsten halogen lamp (ANSI Code DWZ) operated at about 100 watts is preferred.

The center wavelength of the kaolinite measurement band is selected from the aforementioned peak absorption ranges for the two types of structural hydroxyls of kaolinite.

However, the precision of these indications will vary with the uniformities of fiber and water content. To compensate for this effect, third and fourth filters (not shown) may be provided to derive indications of fiber content. This would enable measurement of the two kaolinite structural hydroxyls in a manner which corrects for nonuniformity of fiber content. In addition, by selecting the fiber measurement and fiber reference bands so that they have substantially the same sensitivity to absorption to water, errors in the indications of kaolinite hydroxyls of the two distinctive types resulting from differential absorption by water would become acceptably small.

Accordingly, the third and fourth filters may be selected to pass fiber measurement and fiber reference bands centered at about 2.12 and 1.89 microns, respectively.

In operation, the selected narrow bands of radiation are emitted from the lamp 26, time-multiplexed via the rotating filter wheel 40, and directed to the sheet 2. The radiation impinges on the sheet 2 and a portion thereof is unabsorbed by the sheet and is reflected toward the collector 32, and thus to the photodetector 28. Consequently, the photodetector 28 produces an electrical response (indicated by line 60), typically a voltage, for each selected narrow band of radiation. Each such response 60 is indicative of the intensity of radiation reflected form the sheet 2 toward the photodetector 28 for the narrow band of radiation with which the response is associated.

The reflectance of any particular band of radiation is typically represented mathematically as a stored representation of the detector response obtained during a standardization procedure in which the flag 50 is positioned in the radiation path 56 and the selected bands of radiation are reflected from the diffuse surface 58 toward the photodetector 28.

Referring again to FIG. 1, the detector responses 60 are serially communicated as voltage pulses to a signal processing system (indicated by the line 62). The signal processing system 68 typically includes a conventional ratio analyzer 70 and a computer 72. The signal processing system 68 employs the detector response 62 to calculate measurements of the ratio of the first type of structural hydroxyl of the kaolinite clay platelets from the second type.

The ratios are compared to a target value stored in the computer 62. In response to a deviation from the target value, control signals 64 may be communicated from the computer 62 to a process control actuator 66, which may be any conventional actuator for controlling the amount of doctoring at station 68 or other function which determines clay platelet "flatness" or orientation and therefore, printability.

While the invention has been described according to the preferred embodiment, it is clear that numerous modifications can be made without departing from the spirit and scope of the invention. For example, although some means for modulating radiation emitted from the source will be desirable in any design, the combination of a filter wheel with a single detector can be replaced with plural detectors or multiple-channel detectors in which optical filters corresponding to the selected narrow bands are installed. In addition, although a reflection geometry is indicated and preferred, the sensor can be modified to employ a transmission geometry. Thus, the above description is not intended to restrict the scope of the invention beyond that defined by the following claims and their equivalents.

I claim:

1. A sensor for infrared analysis of paper printability, the paper being a kaolinite clay coated sheet with its printability dependent upon the flatness of kaolinite alumino-silicate clay platelets on the surface thereof, which flatness can be determined by calculating the ratio of the absorption bands from two specific types of structural hydroxyls which are characteristic of kaolinite clay platelet crystals, namely, a first type of hydroxyls whose internuclear axes are inclined toward vacant octahedral crystal positions relative to the kaolinite clay's silicate plate and a second type of hydroxyls where internuclear axes are normal to the silicate plate, said sensor comprising:

a source housing containing a radiation source that emits infrared radiation over a spectral band which includes a plurality of selected narrow bands, the plurality including a first band of measurement radiation having a center wavelength selected from a peak absorption range for said first type of hydroxyls, and a second band of measurement radiation having a center wavelength selected from a peak absorption range for said second type of hydroxyls, a detector housing for receiving radiation emitted from the source after the radiation has interacted with the clay platelets on the surface of the coated sheet, means responsive to said first and second bands of radiation for producing separate electrical indications for each of the two bands of the intensity of radiation that has interacted with the clay platelets on the surface of the coated sheet and for producing a signal indicative of clay platelet flatness.

2. The sensor of claim 1 in which the means for producing separate electrical indications and for producing a signal indicative of clay platelet flatness includes a signal processing system.

3. The signal processing system of claim 2 which includes means to calculate the ratio of the two separate electrical indications to produce the signal indicative of clay platelet flatness.

4. The method of measuring the relative flatness of kaolinite clay platelets on a substrate by use of two separate types of characteristic structural hydroxyls of the kaolinite, said method comprising the combination of procedural steps of:

measuring the radiation absorption of each of the two types of structural hydroxyls and calculating the ratio of one to the other to determine relative flatness of the clay platelets on the substrate surface.

* * * * *